(12) United States Patent  
Hajianpour (10) Patent No.: US 6,506,194 B1  
(45) Date of Patent: Jan. 14, 2003

(54) MEDULLARY PLUG INCLUDING AN EXTERNAL SHIELD AND AN INTERNAL VALVE

(76) Inventor: Mohammed Ali Hajianpour, 1706 Vestal Dr., Coral Springs, FL (US) 33071

( * ) Notice: Subject to any disclaimer, the term of this patent is extended or adjusted under 35 U.S.C. 154(b) by 174 days.

(21) Appl. No.: 09/590,039

(22) Filed: Jun. 8, 2000

(51) Int. Cl.[7] ................................................ A61B 17/72
(52) U.S. Cl. ......................................... 606/95; 606/92
(58) Field of Search ........................ 606/92–95, 62–63, 606/200, 195; 623/23.2, 23.48

(56) References Cited

U.S. PATENT DOCUMENTS

| | | | | |
|---|---|---|---|---|
| 3,834,394 A | * | 9/1974 | Hunter et al. ................ | 604/907 |
| 4,276,659 A | * | 7/1981 | Hardinge ..................... | 606/95 |
| 4,395,806 A | * | 8/1983 | Wonder et al. ............... | 29/424 |
| 4,441,495 A | * | 4/1984 | Hicswa ........................ | 604/103 |
| 4,462,394 A | * | 7/1984 | Jacobs ......................... | 606/192 |
| 4,627,434 A | * | 12/1986 | Murray ........................ | 606/63 |
| RE32,348 E | * | 2/1987 | Pevsner ....................... | 128/325 |
| 4,697,584 A | | 10/1987 | Haynes ........................ | 606/95 |
| 5,084,061 A | * | 1/1992 | Gau et al. .................... | 604/103 |
| 5,181,921 A | * | 1/1993 | Makita et al. ............... | 604/247 |
| 5,222,970 A | * | 6/1993 | Reeves ........................ | 604/164.05 |
| 5,383,932 A | | 1/1995 | Wilson et al. ................ | 623/16 |
| 5,468,245 A | * | 11/1995 | Vargas, III ................... | 606/192 |
| 5,662,657 A | | 9/1997 | Carn ........................... | 606/95 |
| 5,662,712 A | * | 9/1997 | Pathak et al. ................ | 606/195 |
| 5,730,734 A | * | 3/1998 | Adams et al. ................ | 604/167.02 |
| 5,766,178 A | | 6/1998 | Michielli et al. ............. | 606/95 |
| 5,766,203 A | * | 6/1998 | Imran et al. ................. | 604/103.05 |
| 5,782,917 A | | 7/1998 | Carn ........................... | 623/16 |
| 5,827,289 A | | 10/1998 | Reiley et al. ................. | 606/86 |
| 5,849,014 A | | 12/1998 | Mastrorio et al. ........... | 606/94 |
| 5,861,043 A | | 1/1999 | Carn ........................... | 623/16 |
| 5,879,403 A | | 3/1999 | Ostiguy et al. .............. | 623/22 |
| 5,935,169 A | | 8/1999 | Chan ........................... | 623/16 |
| 5,972,034 A | | 10/1999 | Hoffmann et al. ........... | 623/23 |
| 5,997,580 A | | 12/1999 | Mastrorio et al. ........... | 623/22 |
| 6,042,380 A | * | 3/2000 | De Rowe ..................... | 433/172 |
| 6,280,456 B1 | * | 8/2001 | Scribner et al. ............. | 606/192 |
| 6,280,457 B1 | * | 8/2001 | Wallace et al. .............. | 606/191 |
| 6,293,960 B1 | * | 9/2001 | Ken .............................. | 606/195 |
| 6,312,405 B1 | * | 11/2001 | Meyer et al. ................. | 205/363 |
| 2001/0012951 A1 | * | 8/2001 | Bates et al. .................. | 606/200 |
| 2002/0022860 A1 | * | 2/2002 | Borillo et al. ............... | 606/200 |

* cited by examiner

*Primary Examiner*—David O. Reip  
*Assistant Examiner*—D. Jacob Davis  
(74) *Attorney, Agent, or Firm*—Ronald V. Davidge (57) ABSTRACT

A plug for stopping the flow of bone cement in a channel within bone, such as the intramedullary bone canal or a previously prepared channel, includes an elastomeric inflatable structure protected from bone fragments and sharp edges by a shield extending around distal and peripheral sides of the inflatable structure. This inflatable structure is preferably formed as a sleeve extending around a core. The shield includes a distal end fastened to the core and a flexible portion expandable with inflation of the inflatable structure. The core is also removably connected to an insertion tool, with passageways in the insertion tool and in the core being used to insert a fluid into the inflatable structure. A valve extends as a sleeve around the core, and over the passageway, allowing fluid to flow into the inflatable structure, but preventing it from flowing out of the inflatable structure.

20 Claims, 5 Drawing Sheets

MEDULLARY PLUG INCLUDING AN EXTERNAL SHIELD AND AN INTERNAL VALVE

BACKGROUND INFORMATION

1. Field of Invention

This invention relates to medical apparatus for use in the implantation of a joint prosthesis to the end of a bone and, more particularly, to a plug for stopping the flow of bone cement, used in the attachment of a prosthesis, at a predetermined point within the intramedullary bone channel.

3. Description of the Related Art

A number of U.S. Patents describe apparatus for plugging the open end of an intramedullary bone canal to restrict the flow of bone cement during the insertion of bone cement, particularly during the pressurized injection of such a cement during an operative procedure involving the fixation of the stem of an artificial joint prosthesis to the end of a bone such as in the fixation of a hip joint prosthesis to the proximal femur.

For example, U.S. Pat. No. 4,697,584 describes an inflatable bone plug which is inflated with a fluid capable of escaping from the plug within a relatively short period of time after the bone cement holding the prosthesis in place has hardened to avoid possible weakening of the cortical bone surrounding the inflated plug. This invention also relates to an inflatable bone plug of the above type which is preferably constructed from a silicone elastomer and is pressurized with carbon dioxide gas. However, for substantial inflation to occur in the desired manner, the bone plug is made of an elastomeric material. Such materials, which have elastic properties allowing substantial elongation, are subject to cutting and puncturing due to bone splinters and sharp edges in a channel cut into bone, as the plug is moved into position within the channel. Furthermore, the use of an internal valve associated with a needle for injecting a fluid complicates the manufacture of the inflatable bone plug.

U.S. Pat. No. 5,849,014 describes a cement restrictor system including an inflatable body, a conduit having first and second ends that defines a fluid passage to and from the inflatable body, and a shield releasably securable to the conduit. In an exemplary method of making a cement plug with the system an obstruction, such as the shield, is placed in a medullary canal of a long bone beyond the isthmus of the long bone. The obstruction is held in place with the inflatable body. A predetermined quantity of bone cement is poured into the medullary canal and localized by the obstruction. The bone cement is allowed to harden; and the conduit and inflatable body are removed from the bone. Again, the inflatable body is elastomeric and is not protected from cutting or puncturing by bone splinters and sharp edges as the restrictor system is moved into place within a bone channel, with the inflatable body preceding the shield. Also, the separate formation of a bone plug from cement and subsequent removal of the conduit and inflatable body to allow insertion of the prosthesis may lengthen the time required for a hip replacement procedure.

U.S. Pat. No. 5,935,169 describes a bone cement plug including a core having a substantially cylindrically-shaped base portion defining a threaded bore therein extending axially and distally from a proximal end of the base portion; a first leg portion depending from and extending distally from the base portion; and a second leg portion depending from and extending distally from the base portion and opposed to the first leg portion; the base portion threaded bore being adapted to receive an expander screw to wedge apart the first and second leg portions, whereby to expand the core widthwise to secure the plug in the bone canal; and the expander screw, the screw comprising a generally cylindrically-shaped body having a tapered distal end, and a proximal end in which is disposed a threaded bore, external threads disposed on the body, and an annular flange extending outwardly from the proximal end of the body, the screw being threadedly engageable with the core threaded bore for advancement of the screw into the plug for the wedging apart of the first and second legs. A method is also disclosed for using the bone cement plug to compact bone cement into a bone canal during total joint replacement surgeries. However, this type of bone cement plug, having a finite number, such as two, mechanically coupled legs to expand, cannot have the flexibility of a system using an inflatable plug in terms of forming a proper seal within a bone channel which may not be round and smooth, and which varies locally in radius.

U.S. Pat. No. 5,997,580 describes a cement restrictor including a member or body that is expandable or transitionable from a first diameter to a second diameter. The cement restrictor includes a single or multiple finned body having a first stable state and a second stable state. In the first stable state, the cement restrictor is narrower than in the second stable state. While the cement restrictor is readily transitionable from the first stable state to the second stable state, the transition can be irreversible. An illustrative embodiment of the cement restrictor includes a body having a first end and a second end. Bistable fins extend radially from the body and are irreversibly movable from a first stable state to a second stable state. The fins are concave with respect to the first end of the body in the first stable state and convex with respect to the first end of the body in the second stable state. The diameter of each fin is larger in the second stable state than in the first stable state. Other embodiments of inventive cement restrictors are shown that include shape memory material that changes shape or dimension(s) in response to temperature and/or stress. However, the expansion of the cement restrictor is limited to the transition between the first stable state and the second stable state, together with elastic and plastic deformation of the material. This method thus does not offer the kind of flexibility of a system with an inflatable body in expansion to meet varying conditions within the bone channel. Furthermore, the time required to apply liquids at different temperatures to make the transitionable body perform as desired may increase the time required for hip replacement surgery.

A number of patents describe bone plugs including a central core from which a number of disks extend as fins at spaced locations. Examples of such devices are found in U.S. Pat. Nos. 5,383,932, 5,662,657, 5,766,178, 5,782,917, 5,861,043, 5,879,403. Such systems allow only deformation of the individual disks to compensate for changes in the shape of the bone channel, such as out-of-round conditions and changes in hole diameter. Therefore, such systems cannot compensate for such conditions to the extent possible with systems including inflatable bodies.

SUMMARY OF THE INVENTION

It is therefore a first objective of the present invention to provide a bone plug having an elastomeric inflatable structure which is protected from puncture by bone splinters and sharp bone edges by a flexible but tough shield extending around the inflatable structure as it is inserted within a bone channel.

It is a second objective of the present invention to provide a bone plug having a shield structure which can expand greatly without significantly stretching the material from which it is made.

It is a third objective of the present invention to provide a bone plug having an elastomeric inflatable structure which is easily manufactured.

It is a fourth objective of the present invention to provide a bone plug and an associated insertion tool which are easily disconnected when the bone plug has been inserted into a proper position.

According to a first aspect of the present invention, there is provided apparatus for plugging a channel within a bone to stop the flow of bone cement through the channel. The apparatus includes a bone plug and an elongated insertion tool. The bone plug, which is insertable within the channel, includes an inflatable structure, a core attached to the inflatable structure, having a distal portion extending beyond a distal end of the inflatable structure, a shield extending from the distal portion of the core outwardly around and along the inflatable structure, and a valve admitting a fluid into the inflatable structure and preventing a flow of the fluid from the inflatable structure. The core includes a core passageway for the fluid injected into the inflatable. The shield, which expands with inflation of the inflatable structure, is substantially more resistant to damage from sharp objects than the inflatable structure. The elongated insertion tool is removably connected to the core, wherein the elongated insertion tool includes a tool passageway for the fluid injected into the core passageway.

DESCRIPTION OF THE INVENTION

Figures 1, 2:
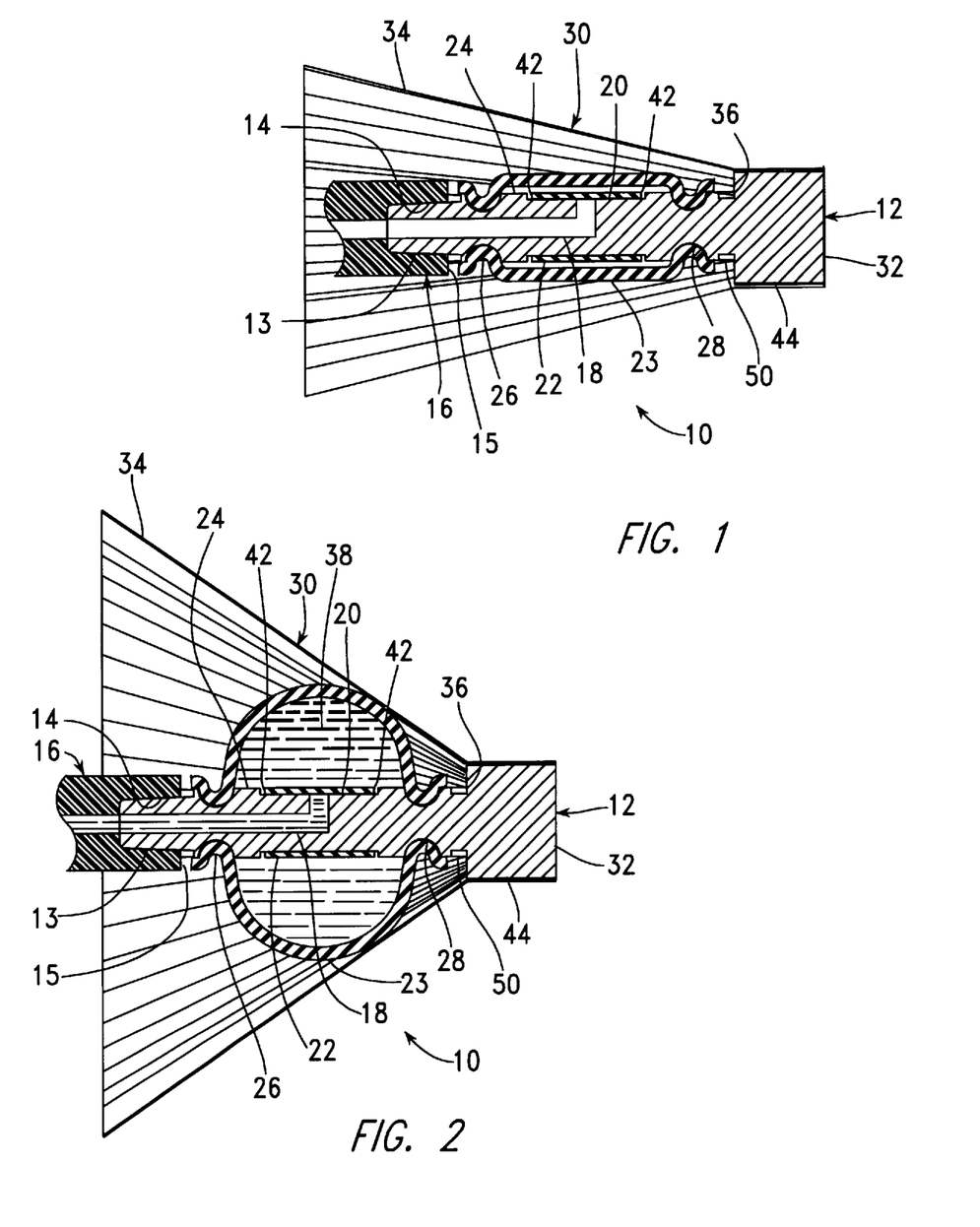
FIG. 1 is a longitudinal cross-sectional view of a bone plug made in accordance with a first embodiment of the present invention with an inflatable sleeve of the bone plug in a fully deflated condition.
FIG. 2 is a longitudinal cross-sectional view of the bone plug of FIG. 1, with the inflatable sleeve in a fully inflated condition.

FIG. 1 is a longitudinal cross-sectional view of a bone plug, generally indicated as 10, made in accordance with the present invention. The bone plug 10 includes a generally cylindrical core 12 having a tapered proximal end 13 which is removably attached to a mating tapered hole 14 at a distal end 15 of an insertion device, generally indicated as 16. The core 12 includes an "L"-shaped internal passage 18, extending between the tapered proximal end 13 and a cylindrical surface 20 extending under an elastomeric valve sleeve 22. The core 12 is preferably composed of a molded thermoplastic material such as acetal or high-density polyethylene. A generally cylindrical inflatable elastomeric sleeve 23 extends along a central portion 24 of the core 12, being held in place by internal ridges 26, which extend within grooves 28 in the core 12. The grooves 28 extend around the circumference of the core 12. The internal ridges 26 may also be attached by means of an adhesive within the grooves 28. The bone plug 10 also includes a shield 30 fastened, preferably by ultrasonic welding or by means of an adhesive, to a cylindrical distal end 32 of the core 12. A conical portion 34 of the shield 30 is expandable and compressible from the undeflected condition in which it is shown in FIG. 1.

Preferably, a specific provision is made to make the bone plug 10 visible during X-ray examination. For example, a stainless-steel ring 36 is included as an insert in the mold making the core 12. Alternately, a radiopaque coating may be applied to a portion of the core 12, or radiopaque fillers may be molded into the core 12. During installation of the bone plug 10 into a cannel within bone, X-ray examination may be used to determine if the correct placement of the plug 10 has been achieved.

FIG. 2 is a longitudinal cross-sectional view of the bone plug 10 with the inflatable elastomeric sleeve 23 in a fully inflated condition. The inflation of the elastomeric sleeve 23 within the conical portion 34 of the shield 30 causes this portion 34 to expand as shown in FIG. 2. When the bone plug 10 is inserted within a bone channel during actual use, the bone channel limits the expansion of the conical portion 32 of the shield 30, causing its deflection into a partially cylindrical shape. At any level of inflation, the shield 30 extends around the inflatable elastomeric sleeve 23, protecting it from bone splinters or other sharp edges of a channel within the bone.

After the bone plug 10 is inserted into a bone channel, the inflatable elastomeric sleeve 23 is filled with a biocompatible fluid 38, such as saline solution, causing the sleeve 23 to extend from the uninflated condition of FIG. 1 to the inflated condition of FIG. 2. This inflation is accomplished by injecting the fluid 38 through the internal passage 18, so that pressure of the fluid 38 spreading between the cylindrical surface 20 of the core 12 and an internal surface 40 of the elastomeric valve sleeve 22 causes the expansion of the valve sleeve 22. This expansion allows the release of the fluid 38 past the ends 42 of the valve sleeve 22. When the pressure causing the injection of the fluid 38 through the internal passage 18 is stopped, the valve sleeve 22 closes, reducing the stresses previously causing its expansion, and preventing flow of the fluid 38 in either direction past the valve sleeve ends 42. In this way, the valve sleeve 22 acts as an internal check valve.

Thus, the inflatable elastomeric sleeve 23, together with the core 12, provide an inflatable structure which can be easily molded using conventional techniques, being removable from a central die or mandrel. The valve sleeve 22 is also easily molded. There is no need to form an enclosed structure with an internal valve, in the manner of the prior art device described in U.S. Pat. No. 4,697,584.

Figure 3:
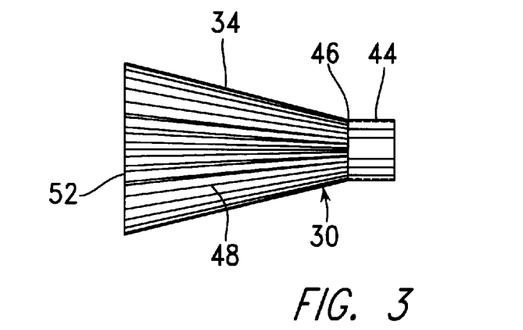
FIG. 3 is a side elevation of a shield of the bone plug of FIG. 1 in an undeflected condition.
Figure 4:
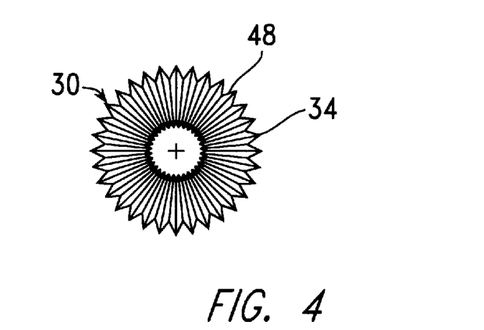
FIG. 4 is a proximal end elevation of the shield of FIG. 3 in an undeflected condition.

FIGS. 3 and 4 show the shield 30 in an undeflected condition (i.e. in the shape resulting from the manufacturing process, such as molding, with which it is made). FIG. 3 is a side elevation of the shield 30, while FIG. 4 is a proximal end elevation thereof.

Referring to FIGS. 1, 3, and 4, The shield 30 includes a distal cylindrical portion 44, which is attached to the distal end 32 of the core 12 (shown in FIG. 1) and a pleated conical portion 34, which extends outward in the undeflected condition at an included angle of, for example, 28 degrees. At the transition 46 between the cylindrical portion 44 and the conical portion 34, the pleats 48 extend inward, into a reduced-diameter cylindrical portion 50 of the core. The width of the individual pleats 48 increases linearly toward the proximal end 52 of the shield 30, providing more material to allow the conical portion 34 to be expanded. For example, each individual pleat 48 has a width of 0.76 mm (0.03 in.) at the transition 46, increasing to a width of 2.5 mm (0.10 in.) at the proximal end 52. The shield 30 is preferably molded from a flexible but tough material, such as polypropylene or a polyester resin, having a wall thickness of 0.25 mm (0.01 in.).

Figure 5:
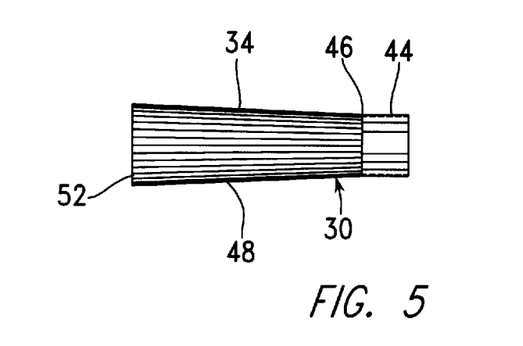
FIG. 5 is a side elevation of the shield of FIG. 3 in a fully compressed condition.
Figure 6:
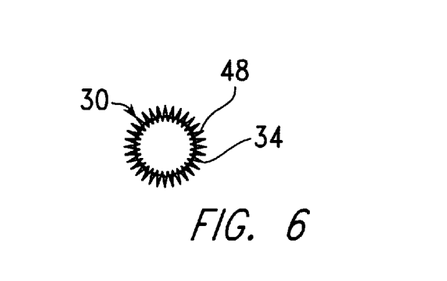
FIG. 6 is a proximal end elevation of the shield of FIG. 3 in a fully compressed condition.

FIGS. 5 and 6 show the shield 30 in a fully compressed condition, with FIG. 5 being a side elevation and with FIG. 6 being a proximal end elevation. In the fully compressed condition, the pleated conical portion 34 extends outward at an included angle of, for example, 5 degrees. The shield 20 is compressed by the application of external forces, such as the forces produced as the bone plug 10 is slid into a gradually narrowing bone canal.

Figure 7:
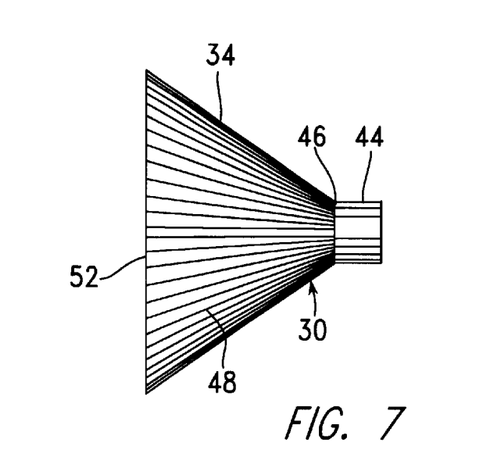
FIG. 7 is a side elevation of the shield of FIG. 3 in a fully extended condition.
Figure 8:
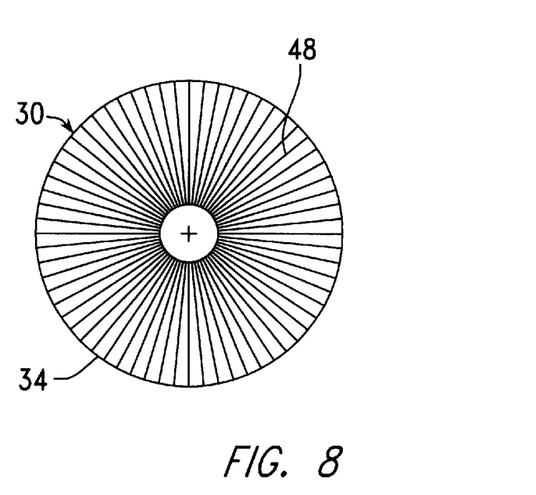
FIG. 8 is a proximal end elevation of the shield of FIG. 3 in a fully extended condition.

FIGS. 7 and 8 show the shield 30 in a fully extended condition, with FIG. 7 being a side elevation and with FIG. 8 being a proximal end elevation. In the fully extended condition, the pleated conical portion 34 outward at an included angle of, for example, 70 degrees. At the proximal end 52, the pleats 48 are essentially unfolded. The shield 20 is extended by the application of a force from within the pleated conical portion 34, as the inflatable elastomeric sleeve 23 is inflated.

Thus, the pleated conical shape of the proximal portion 34 allows a tough but flexible material to be used to form the shield 30. For the inflatable sleeve 23, an elastomeric material is used to allow the stretching necessary to accommodate the desired change in shape. Elastomeric materials are by nature relatively easily torn by sharp objects, such as bone splinters and other sharp edges which may protrude from the previously-prepared hole in a bone. The shield 30 thus provides substantial protection for the inflatable sleeve 23, being made of a material which is much more resistant to piercing or tearing by splinters and sharp edges.

Figures 9, 10:
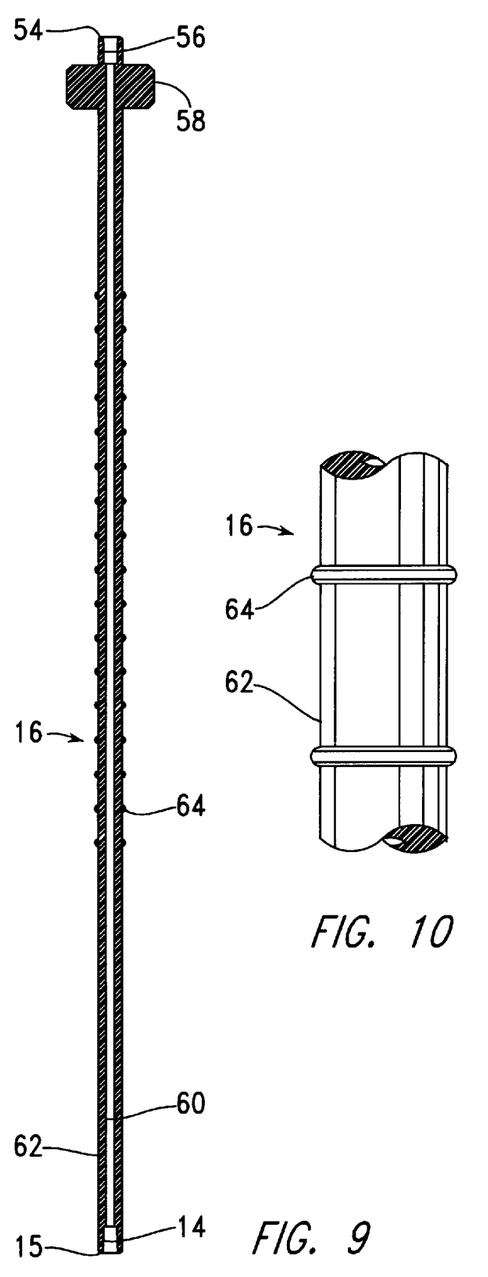
FIG. 9 is a longitudinal cross-sectional elevation of an insertion device used to insert the bone plug of FIG. 1 into a previously-prepared channel within a bone.
FIG. 10 is a fragmentary side elevation of the insertion device of FIG. 9.

FIG. 9 is a longitudinal cross-sectional elevation of the insertion device 16 used to insert the bone plug 10 of FIG. 1 into a previously-prepared channel within a bone. Referring to FIGS. 1 and 9, the distal end 15 of the insertion device 16 includes a tapered hole 14 for removably receiving the tapered end 13 of the bone plug 10. The proximal end 54 of the insertion device 16 includes a tapered hole 56, for removably receiving the tapered end of a conventional syringe, and a cylindrical knob 58 to facilitate handling the insertion device 16. The knob 58 may have a grooved or knurled outer surface. The insertion device 16, which is preferably molded from a thermoplastic resin, also includes a longitudinally extending hole 60, through which the fluid 38 is injected into the bone plug 10.

FIG. 10 is a fragmentary side elevation of the insertion device 16 of FIG. 9. Referring to FIGS. 9 and 10, the outer cylindrical surface 62 of the insertion device 16 includes a number of spaced-apart ribs 64, which are used to determine how far the insertion device 16 is inserted into a channel within bone. Preferably, the first rib 64, closest to the distal end 15, is 120 mm (4.73 in.) from the distal end 15, and sixteen additional ribs 64 extend from this rib 64 toward the proximal end 54 of the insertion device 16, being spaced along the length of the insertion device 16 at center-to-center distances of 10 mm (0.394 in.).

Figure 11:
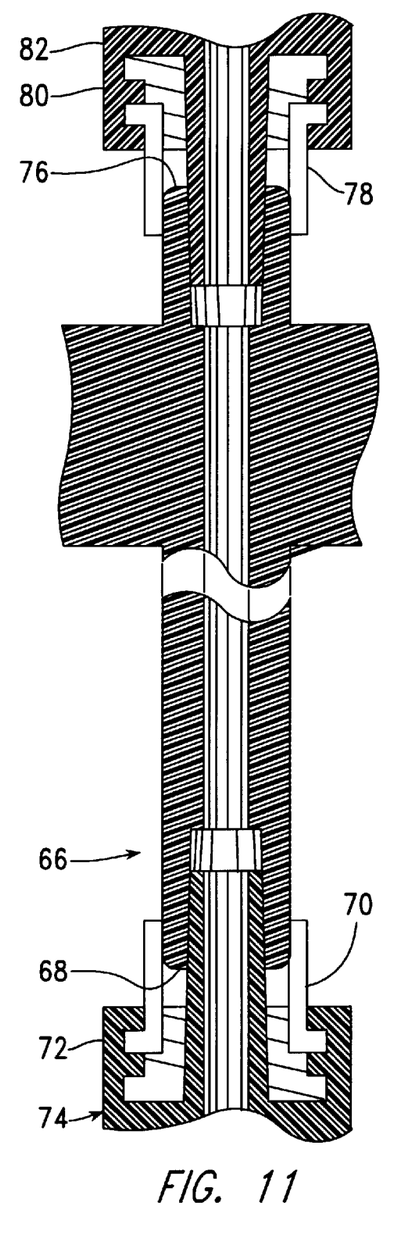
FIG. 11 is a fragmentary longitudinal cross-sectional elevation of an alternative insertion device used to insert the bone plug of FIG. 1 into a previously-prepared channel within a bone.

FIG. 11 is a fragmentary longitudinal cross-sectional elevation of an alternative version 66 of an insertion device. This alternative version 66 is similar to the insertion device 16, except that the distal end 68 is extended to include a pair of tabs 70 engaging an internally threaded section 72 of an alternative version 74 of the bone plug, and the proximal end 76 is similarly extended to include a pair of tabs 78 engaging a conventional internally threaded section 80 of a syringe 82. This alternative construction may be applied to either end of the insertion device, or to both ends, as shown in FIG. 11.

Figure 12:
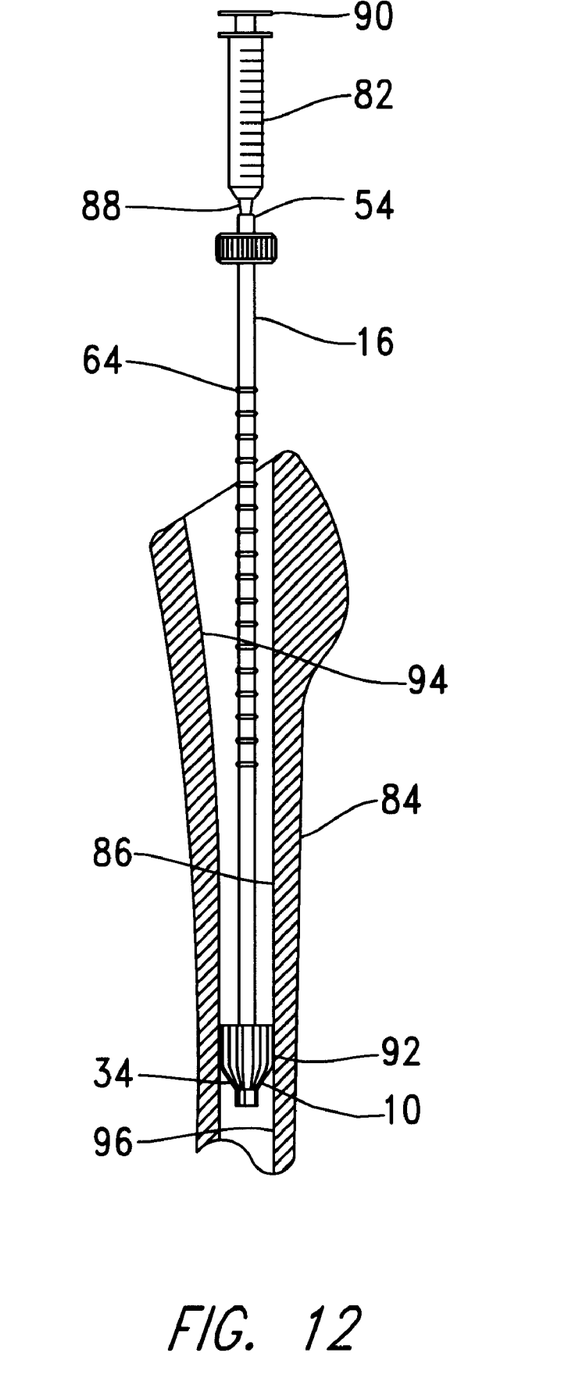
FIG. 12 is a longitudinal cross-sectional elevation of a femur including a previously-prepared channel, showing the insertion and inflation of the bone plug of FIG. 1 with the insertion device of FIG. 9.

FIG. 12 is a longitudinal cross-sectional elevation of a femur 84, including a previously-prepared channel 86, showing the insertion and inflation of the bone plug 10 of FIG. 1 with the insertion device 16 of FIG. 9. Referring to FIGS. 1 and 12, before this process is begun, the bone plug 10 is fastened to the distal end 15 (shown in FIG. 9) of the insertion device 16, with the bone plug 10 and the insertion device 16 being twisted relative to one another so that the tapered proximal end 13 of the bone plug 10 firmly engages the tapered hole 14 within the insertion device 16. Similarly, the syringe 82, filled with the fluid 38 used for inflating the inflatable elastomeric sleeve 23, is attached to the proximal end 54 of the insertion device 16, being twisted relative to the insertion device 16 so that a conventional tapered end 88 firmly engages the tapered hole 56 within the insertion tool 16.

Next, the insertion tool 16 is used to push the bone plug 10 into place, with the ribs 64 providing a visual indication of the depth to which the bone plug 10 is inserted. When the desired depth is reached, the plunger 90 of the syringe 82 depressed to inject the fluid 38 into the inflatable elastomeric sleeve 23 of the bone plug 10. Within the bone plug 10, the resulting inflation of the sleeve 23 pushes the pleated conical portion 34 of the shield 30 outward, to be held against the bone channel 86. A distal part 92 of the pleated conical portion 34 is forced into an essentially cylindrical configuration by contact with the channel 86, as flexure of the pleated conical portion occurs around the inflated elastomeric sleeve 23. After the bone plug 10 has been inflated in place, as shown in FIG. 12, the insertion tool 16 is twisted to unlock its connection with the bone plug 10, and the insertion tool 16 is removed. Then the prosthesis (not shown) is placed within the upper portion 94 of the bone channel 86, and the remaining space within this upper portion 94 is filled with bone cement. The presence of the bone plug 10 prevents the migration of this bone cement into the lower portion 96 of the bone channel 86.

The process of curing bone cement is exothermic, causing the local temperature to raise. In certain cases, this temperature increase may cause the formation of steam from the fluid 38 within the inflatable elastomeric sleeve 23. This sleeve 23 is preferably made to rupture in this event, so that extreme increases in pressure will not be transferred to surrounding bone. When the temperature has reached a such a high level, the surrounding bone cement has sufficiently hardened to make continued pressure within the inflatable sleeve 23 unnecessary to prevent leakage of cement around the plug 10.

Figure 13:
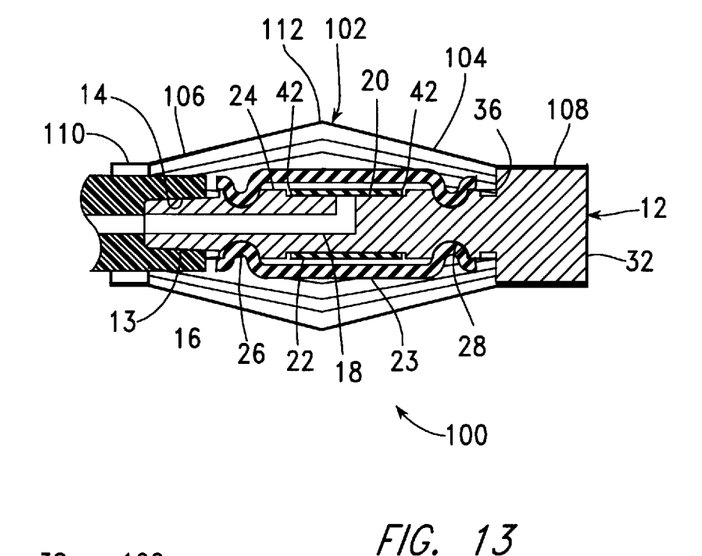
FIG. 13 is a longitudinal cross-sectional view of a bone plug made in accordance with a second embodiment of the present invention with an inflatable sleeve of the bone plug in a fully deflated condition.
Figure 14:
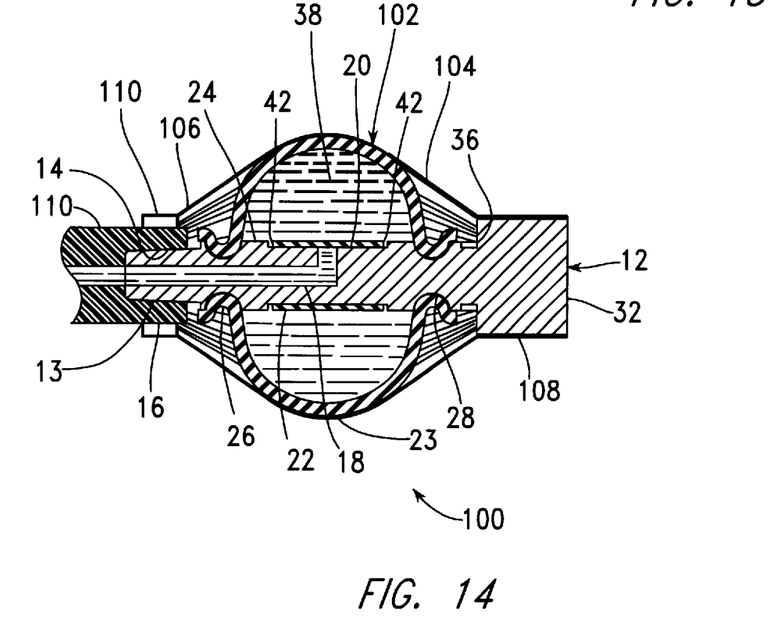
FIG. 14 is a longitudinal cross-sectional view of the bone plug of FIG. 13, with the inflatable sleeve in a fully inflated condition.

FIGS. 13 and 14 are longitudinal cross-sectional views of a second embodiment 100 of a bone plug built in accordance with the present invention. FIG. 13 shows the bone plug 100 with the inflatable elastomeric sleeve 23 in a deflated condition, while FIG. 14 shows the bone plug 100 with the sleeve in a fully deflated condition. This second embodiment 100 is similar to the first embodiment 10, with like parts being accorded like reference numerals, except that, in the second embodiment 100, the shield 30 having a single pleated conical section 34 is replaced by an alternative shield 102 having a distal pleated conical section 104 and a proximal pleated conical section 106. These pleated conical sections 104, 106 meet at their maximum openings, with the entire shield 102, including the conical sections 104, 106, preferably being made as a single part, together with a distal cylindrical section 108 and a proximal conical section 110. A forming process such as blow molding can be used to make the use of an internal die unnecessary.

During inflation of the elastomeric sleeve 23, flexure occurs in the region 112 of the shield 102, but there is no need to form the proximal half portion of the pleated section into a cylindrical shape, as discussed above in reference to FIG. 12. The distal cylindrical section 108 of the shield 100 is attached to the distal cylindrical portion 32 of the core 12. The proximal cylindrical section 110 of the shield 100 is allowed to slide along the insertion tool 16 with inflation of the elastomeric sleeve 23.

While the present invention has been described in its preferred forms or embodiments with some degree of particularity, it is understood that this description has been given only by way of example and that numerous changes in the details of construction, fabrication, and use, including changes in the combination and arrangement of parts, may be made without departing from the spirit and scope of the invention.

I claim:

1. Apparatus for plugging a channel within a bone to stop the flow of bone cement through said channel, wherein said apparatus comprises: a bone plug insertable within said channel, wherein said bone plug includes an inflatable structure, a core attached to said inflatable structure, wherein said core includes a distal portion extending beyond a distal end of said inflatable structure, a shield extending from said distal portion of said core outwardly around and along said inflatable structure, and a valve admitting a fluid into said inflatable structure and preventing a flow of said fluid from said inflatable structure, wherein said core includes a core passageway for said fluid injected into said inflatable structure, and wherein said shield expands with inflation of said inflatable structure, and wherein said shield is substantially more resistant to damage from sharp objects than said inflatable structure; and an elongated insertion tool removably connected to said core, wherein said elongated insertion tool includes a tool passageway for said fluid injected into said core passageway.

2. The apparatus of claim 1, wherein said inflatable structure extends as a sleeve over said core, being fastened to said core at proximal and distal ends of said inflatable structure.

3. The apparatus of claim 2, wherein
said valve extends as a sleeve over said core passageway within said inflatable structure, blocking movement of said fluid from said inflatable structure into said core passageway, and
said fluid flows through said sleeve and out an end of said sleeve into said inflatable structure from said core passageway.

4. The apparatus of claim 3, wherein said valve is composed of an elastomer.

5. The apparatus of claim 2, wherein
a distal portion of said core extends past said distal end of said inflatable structure,
said shield includes a distal portion fastened to said distal portion of said core and a flexible portion extending over said inflatable structure.

6. The apparatus of claim 5, wherein said flexible portion includes a pleated shape.

7. The apparatus of claim 6, wherein said flexible portion includes a first conical portion extending from said distal portion of said shield, with an enlarged end of said first conical portion at a proximal end of said first conical portion.

8. The apparatus of claim 7, wherein said flexible portion extends around an entire length of said inflatable structure.

9. The apparatus of claim 7, wherein said flexible portion additionally includes a second conical portion with an enlarged end of said second conical portion extending from said enlarged end of said first conical portion.

10. The apparatus of claim 9, wherein said second conical portion includes a slidable proximal end.

11. The apparatus of claim 1, wherein
said valve extends as a sleeve over said core passageway within said inflatable structure, blocking movement of said fluid from said inflatable structure into said core passageway, and
said fluid flows through said sleeve and out an end of said sleeve into said inflatable structure from said core passageway.

12. The apparatus of claim 1, wherein said elongated insertion tool is additionally removably connected to a syringe for injecting said fluid into sad tool passageway.

13. The apparatus of claim 1, wherein said shield is composed of polypropylene.

14. Apparatus for plugging a channel within a bone to stop the flow of bone cement through said channel, wherein said apparatus comprises:
a bone plug insertable within said channel, wherein said bone plug includes a core, an inflatable structure extending as a sleeve over said core, being fastened to said core at proximal and distal ends of said inflatable structure, and a valve admitting a fluid into said inflatable structure and preventing a flow of said fluid from said inflatable structure, wherein said core includes a core passageway for said fluid injected into said inflatable structure, wherein said valve extends as a sleeve over said core passageway within said inflatable structure, blocking movement of said fluid from said inflatable structure into said core passageway, and wherein said fluid flows through said sleeve and out an end of said sleeve into said inflatable structure from said core passageway; and
an elongated insertion tool removably connected to said core, wherein said elongated insertion tool includes a tool passageway for said fluid injected into said core passageway.

15. The apparatus of claim 14, wherein a distal portion of said core extend past said distal end of said inflatable structure, and said bone plug additionally includes a shield extending outwardly around and along said inflatable structure.

16. The apparatus of claim 15, wherein said shield includes a distal portion fastened to said distal portion of said core and a flexible portion extending over said inflatable structure.

17. The apparatus of claim 16, wherein said flexible portion includes a pleated shape.

18. The apparatus of claim 17, wherein said flexible portion includes a first conical portion extending from said distal portion of said shield, with an enlarged end of said first conical portion at a proximal end of said first conical portion.

19. The apparatus of claim 18, wherein said flexible portion extends around an entire length of said inflatable structure.

20. The apparatus of claim 18, wherein said flexible portion additionally includes a second conical portion with an enlarged end of said second conical portion extending from said enlarged end of said first conical portion.

* * * * *